United States Patent [19]

DeBernardis et al.

[11] Patent Number: 4,505,932
[45] Date of Patent: Mar. 19, 1985

[54] METHOD OF PRODUCING $\alpha_2$-ADRENERGIC RECEPTOR AGONIST ACTIVITY

[75] Inventors: John F. DeBernardis, Lake Villa; David L. Arendsen, Libertyville, both of Ill.

[73] Assignee: Abbott Laboratories, North Chicago, Ill.

[21] Appl. No.: 590,938

[22] Filed: Mar. 19, 1984

Related U.S. Application Data

[63] Continuation-in-part of Ser. No. 494,230, May 13, 1983, abandoned.

[51] Int. Cl.³ .................. A61K 31/135; C07C 91/42
[52] U.S. Cl. .................................... 514/649; 564/387
[58] Field of Search ..................... 564/387; 424/330

[56]  References Cited
U.S. PATENT DOCUMENTS 3,419,560  12/1968  Bernstein et al. .................. 564/287

FOREIGN PATENT DOCUMENTS 2500823  9/1982  France .
53-5146   1/1978  Japan ................................. 564/387

OTHER PUBLICATIONS

Chem. Abstracts, 98:10712f (1982).
Heinsimer et al., "Adrenergic Receptors: Biochemistry, Regulation, Molecular Mechanism, and Clinical Implications", J. Lab. Clin. Med. 100(5): 641-658 (1982).

Primary Examiner—Stanley J. Friedman
Assistant Examiner—Joyce L. Morrison
Attorney, Agent, or Firm—Steven F. Weinstock; Martin L. Katz

[57]  ABSTRACT

A method of producing $\alpha_2$-adrenergic receptor agonist activity by contacting an $\alpha_2$-adrenergic receptor with an effective amount of a compound of the formula:

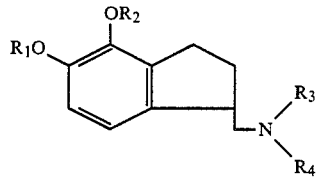

wherein $R_1$, $R_2$, $R_3$ and $R_4$ are independently selected from hydrogen or loweralkyl of 1 or 2 carbon atoms, or a pharmaceutically acceptable salt thereof.

6 Claims, No Drawings

METHOD OF PRODUCING $\alpha_2$-ADRENERGIC RECEPTOR AGONIST ACTIVITY

REFERENCE TO RELATED APPLICATION

This application is a continuation-in-part of U.S. Ser. No. 494,230 filed May 13, 1983, now abandoned.

BACKGROUND OF THE INVENTION

This invention relates to methods of producing $\alpha_2$-adrenergic receptor agonist activity. More particularly, this invention relates to the production of $\alpha_2$-adrenergic receptor agonist activity by contacting an $\alpha_2$-adrenergic receptor with an optionally substituted aminomethyl-4,5-dihydroxy (or alkoxy) indane or a pharmaceutically acceptable salt thereof.

The adrenergic nervous system plays a primary role in the neurogenic regulation of the cardiovascular system. The sympathetic outflow to the heart and peripheral vessels originates from the vasomotor center and travels along descending neuronal pathways interrupted by synapses, the switching units which transmit the neurological signal from higher to lower neurons and from nerve endings to cells of the effector organ. Transmission of the neurological signal across synapses is mediated chemically by a neurotransmitter which is stored in the vesicles of nerve endings. Upon arrival of the neurological signal, regulated quantities of neurotransmitter are released into the synapse where it combines with receptor sites in the cellular membrane of the next neuron or effector ogan, and excites the receptor cell to propagate the neurological signal or to produce an effect in an effector organ.

The principal natural neurotransmitters specific to the adrenergic nervous system are norepinephrine and epinephrine (hereinafter collectively referred to as "norepinephrine"), which mediate neurological transmission in some central noradrenergic neurons in the vasomotor center and elsewhere in the brain as well as peripherally in so-called postganglionic symphathetic neurons. Adrenergic receptors for norepinephine have been recognized to be proteins bound to membranes of effector cells. These receptors control the function of the effector cell, and through it the function of a whole organ or organ systems. Adrenergic receptors are highly specific for norepinephrine and can discriminate between it and may other transmitters and molecules. However, their discrimination capability is not complete, and other related catecholamines as well as various synthetic agents have been found to bind to adrenergic receptors.

Through observed responses of various tissues and organs to norepinephrine and related catecholamine-like compounds, it has been found that the nature of adrenergic receptors differs substantially in different tissues where they mediate different functions. In addition, adrenergic receptors from various tissues have been found to differ in their discriminatory abilities for other compounds. Based on the foregoing and other observations, adrenergic receptors have been classified into at least two major groups, i.e., the $\alpha$-adrenergic receptors and the $\beta$-adrenergic receptors. In addition, the $\alpha$-groups of receptors have been further divided into the $\alpha_1$-adrenergic receptor sub-group and the $\alpha_2$-adrenergic receptor sub-group. The $\alpha_1$-adrenergic receptors have been characterized as being exitatory in nature, primarily functioning to result in peripheral vascular contraction. On the other hand, presynaptic $\alpha_2$-adrenergic receptors have been characterized as being inhibitory in nature, primarily functioning to inhibit transmitter release through inhibition of adenylate cyclase activity, while post-synaptic $\alpha_2$-adrenergic receptors may function to result in peripheral vascular contraction.

Inasmuch as the different groups and sub-groups of adrenergic receptors mediate different functions in different bodily tissues and organs, it is highly desirable to obtain chemical compounds or entities which are highly selective for limited types of receptor sites. In this manner, isolated symptoms can be effectively treated, without affecting other unrelated tissues and organs, by selectively agonizing or antagonizing a particular sub-group of receptor sites.

One compound which has been found to exhibit relatively specific binding affinity for $\alpha_2$-receptor sites is known as clonidine. The structure of clonidine is as follows:

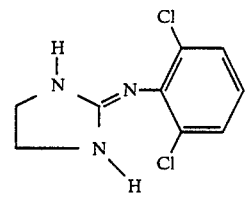

Clonidine has been shown to agonize $\alpha_2$-adrenergic activity and has been used as an antihypertensive agent to regulate $\alpha_2$-mediated functions. Although clonidine has been found to be useful as an $\alpha_2$-adrenergic receptor agonist, the search continues for new compounds having improved properties.

DETAILED DESCRIPTION OF THE INVENTION

The present invention relates to compounds of the formula:

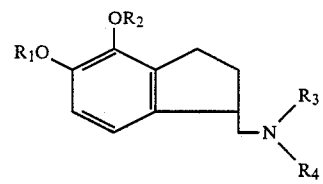

wherein $R_1$, $R_2$, $R_3$ and $R_4$ are independently selected from hydrogen or loweralkyl of 1 to 2 carbon atoms, and the pharmaceutically salts thereof.

In one of its aspects, the invention relates to methods of producing $\alpha_2$-adrenergic receptor agonistic activity comprising contacting an $\alpha_2$-adrenergic receptor with an agonistically effective amount of a compound of formula I.

In yet another one of its aspects, the invention relates to methods of producing $\alpha_2$-adrenergic receptor agonistic activity comprising administering to an animal an $\alpha_2$-adrenergic receptor agonistically effective amount of a compound of formula I.

In yet another one of its aspects, the invention relates to methods of treating hypertension comprising administering to an animal requiring said treatment an antihypertensively effective amount of a compound of formula I.

It has been determined that the compounds of formula I exhibit a high degree of selectivity for $\alpha_2$-adrenergic receptor sites and produce $\alpha_2$-agonism. The compounds are therefore useful in the production of selective $\alpha_2$-agonistic activity and are therapeutically useful, e.g., in the treatment of hypertension. The compounds of formula I wherein $R_1$ and/or $R_2$ are other than hydrogen are also useful as intermediates in the production of the dihydroxy compounds of formula I wherein $R_1$ and $R_2$ are hydrogen.

As used herein, the term "loweralkyl" means straight-chain alkyl groups having 1 or 2 carbon atoms, i.e., methyl or ethyl.

Pharmaceutically acceptable acid addition salts of the compounds of formula I may be formed with organic or inorganic acids by methods well known in the art. For example, the base may be treated with an organic or inorganic acid in an aqueous miscible solvent, such as acetone or ethanol, with isolation of the salt by concentration or cooling, or in an aqueous immiscible solvent, such as ethyl ether or chloroform, or the like. Illustrative salts within the scope of this invention include maleate, fumarate, benzoate, ascorbate, pamoate, succinate, bismethylenesalicylate, methanesulfonate, ethanedisulfonate, benzenesulfonate, acetate, propionate, tartrate, salicylate, citrate, gluconate, lactate, malate, mandelate, cinnamate citraconate, aspartate, stearate, palmitate, itaconate, glyucolate, p-aminobenzoate, glutamate, theophylline acetates, hydrochloride, hydrobromide, sulfate, cyclohexylsulfamate, phosphate, nitrate and similar suitable pharmaceutically acceptable salts.

The compounds of the invention may be synthesized from a 2,3-dialkoxycinnamic acid of the formula:

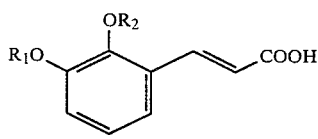

wherein $R_1$ and $R_2$ are loweralkyl of 1 or 2 carbon atoms, according to the following reaction scheme wherein $R_1$ and $R_2$ are represented by a methyl group for purposes of illustration:

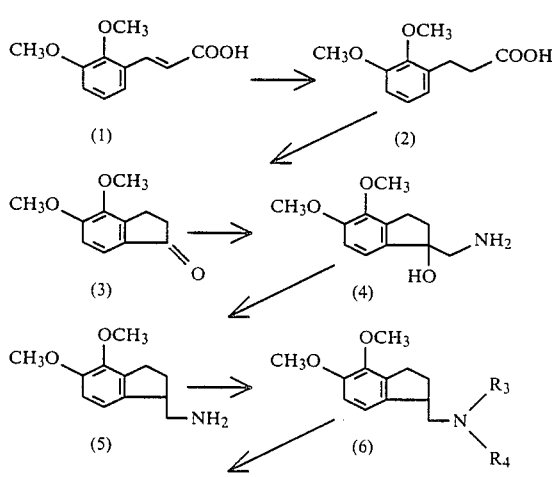

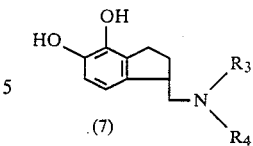

In accordance with the foregoing reaction scheme, a 2,3-dialkoxycinnamic acid (1) is hydrogenated to obtain 3-(2,3-dialkoxyphenyl)propionic acid (2), and then reacted with polyphosphoric acid to obtain 4,5-dialkoxy-1-indanone (3). The indanone (3) is converted to the corresponding 1-aminomethyl-1-hydroxy indane (4) by reaction with trimethylsilyl cyanide, followed by reduction with lithium aluminum hydride. Upon hydrogenation of the latter compound, 1-aminomethyl-4,5-dialkoxy indane (5) is obtained.

To obtain the compounds of formula I wherein $R_3$ and/or $R_4$ are other than hydrogen, the 1-aminomethyl-4,5-dialkoxy indane compound (5) may then be reacted with the suitable aldehyde in the presence of sodium acetate and methanol under hydrogenation conditions to obtain the corresponding 1-N,N-dialkylaminomethyl-4,5-dialkoxy indane compound (6). For example, 1-aminomethyl-4,5-dialkoxy indane is reacted with formaldehyde to obtain the corresponding N,N-dimethyl compound or with acetaldehyde to obtain the N,N-diethyl compound. The dialkoxy indanone (3) may be selectively dealkylated, such as by reaction with aluminum trichloride and methylene dichloride to obtain the corresponding monoalkoxy, monohydroxy compound. Protection of the hydroxyl group, followed by conversion to the corresponding 1-aminomethyl indane as described above, and then deprotection of the hydroxyl group, results in the corresponding monoalkoxy monohydroxy-1-aminomethyl indane.

The mono akoxy or dialkoxy indane compounds of formula I may be O-demethylated or O-de-ethylated, if desired, such as by suspension in methylene chloride and reaction with boron tribromide at reduced temperature, followed by decomposition of excess boron tribromide with methanol, to obtain 1-N,N-dimethylaminomethyl-4,5-dihydroxy indane (7).

The foregoing may be better understood in connection with the following illustrative examples:

EXAMPLE 1

3-(2,3-Dimethoxyphenyl)propionic acid

An aqueous solution was formed of 177 g. of 2,3-dimethoxycinnamic acid and 10.0 g. of 20% palladium-on-carbon catalyst in 1800 ml. of tetrahydrofuran, and was allowed to react under 3 atmospheres of hydrogen at room temperature for one hour. The resulting solution was evaporated in vacuo and dissolved in an approximately equal volume of a saturated aqueous sodium hydroxide solution. The solution was extracted with two approximately equal volume portions of methylene dichloride. The aqueous phases were combined, acidified with 6N hydrochloric acid and extracted with three approximately equal volume portions of methylene dichloride. The combined extracts were washed with an approximately equal volume of a saturated aqueous sodium chloride solution, dried over magnesium sulfate, filtered, evaporated and then dried under vacuum to yield 175.8 g. of 3-(2,3-dimethoxyphenyl)- propionic acid as a white solid. Melting point (M.P.), 61°–63° C.

EXAMPLE 2

4,5-Dimethoxy-1-indanone

A reaction mixture of 14.3 g. of 3-(2,3-dimethoxyphenyl)propionic acid and 128 g. of polyphosphoric acid, was stirred with a glass rod at 85°–87° C. for 10 minutes. The reaction mixture was poured onto approximately 500 g. of ice and stirred for thirty minutes. The mixture was then filtered and the residue was washed with approximately equal volume portions of water, a saturated aqueous sodium hydroxide solution and then water. The residue was dried in vacuo, to yield 8.1 g. of 4,5-dimethoxy-1-indanone as a brown solid. M.P. 73°–74° C.

EXAMPLE 3

1-Aminomethyl-1-hydroxy-4,5-dimethoxy indane

A reaction mixture of 32 g. of 4,5-dimethoxy-1-indanone, 18.9 g. (23.1 ml) of trimethylsilyl cyanide and a catalytic amount of zinc iodide was stirred overnight at 62° C. The reaction mixture was cooled to room temperature and added dropwise to a stirred slurry of 14.8 g. of lithium aluminum hydride in 300 ml. of anhydrous ether. The resulting reaction mixture was refluxed for 2.5 hours and then cooled to 0° C. Excess lithium aluminum hydride was decomposed by adding 15 ml. of water, 15 ml. of a 15% by weight aqueous sodium hydroxide solution and then 45 ml. of water to the reacton mixture, and then stirring the mixture for 30 minutes at room temperature. The mixture was filtered and the residue was washed with methylene dichloride. The filtrate was evaporated and dried in vacuo to yield 34 g. of 1-aminomethyl-1-hydroxy-4,5-dimethoxy indane as a brown solid. This compound was used directly without further purification.

EXAMPLE 4

1-Aminomethyl-4,5-dimethoxy indane hydrochloride

A reaction mixture was formed of 34 g. of 1-aminomethyl-1-hydroxy-4,5-dimethoxy indane, 21.7 ml. of concentrated hydrochloric acid, and 8.2 g. of 5% palladium-on-carbon catalyst in 230 ml. of methanol. The reaction mixture was stirred under 3 atmospheres of hydrogen at room temperature for 16 hours and then at 50° C. for 1 hour. The mixture was filtered, then evaporated to dryness and dried in vacuo to yield 27.1 g. of a tan solid. Recrystallization from ethanol yielded 20.8 g. of 1-aminomethyl-4,5-dimethoxy indane hydrochloride as white crystals. M.P. 225°–230° C.

Analysis calculated: $C=59.14$, $H=7.44$, $N=5.75$. Found: $C=59.00$, $H=7.50$, $N=5.66$.

EXAMPLE 5

1-N,N-Dimethylaminomethyl-4,5-dimethoxy indane hydrochloride

A reaction mixture was formed of 2.0 g. of 1-aminomethyl-4,5-dimethoxy indane hydrochloride, 1.1 g. of sodium acetate trihydrate, 0.76 g. of 5% palladium-on-carbon catalyst, 92 ml. of methanol and 8 ml. of a 37% solution of formaldehyde in water. The reaction mixture was stirred and allowed to react under 3 atmospheres of hydrogen at room temperature for 2 hours. The mixture was filtered, then evaporated to dryness and the residue dissolved in 20 ml. of a 1N aqueous solution of potassium hydroxide. The aqueous solution was extracted with three approximately equal volume portions of methylene dichloride and the resulting extracts were combined. The combined extracts were washed with approximately equal volume portions of water and then a saturated aqueous sodium chloride solution. The washed extract was dried over magnesium sulfate, filtered and stripped in vacuo to yield a colorless oil. The oil was dissolved in a solution of 5 ml. of ethanol, then added to 30 ml. of an ethereal hydrochloric acid solution, filtered, and then dried in vacuo to yield 1.84 g. of 1-N,N-dimethylaminomethyl-4,5-dimethoxy indane hydrochloride as a white solid. M.P. 259°–260° C.

EXAMPLE 6

1-N,N-Dimethylaminomethyl-4,5-dihydroxy indane hydrobromide

A slurry of 1.82 g of 1-N,N-dimethylaminomethyl-4,5-dimethoxy indane hydrochloride in about 45 ml. of methylene dichloride was stirred under nitrogen at $-78°$ C. as a solution of 1.65 ml. of boron tribromide in 6 ml. of methylene dichloride was added dropwise. The resulting reaction mixture was stirred at $-78°$ C. for one hour and then at 0° C. for two hours. The reaction mixture was then cooled to $-78°$ C. and 32 ml. of methanol was added dropwise. The resulting mixture was stirred at $-78°$ C. for thirty minutes and then overnight at room temperature. The mixture was filtered, and the residue was washed with 50 ml. of diethyl ether and dried in vacuo to yield 1.3 g of 1-N,N-dimethylaminomethyl-4,5-dihydroxy indane hydrobromide as a white solid. M.P., 239°–240° C.

Analysis calculated: $C=50.01$, $H=6.30$, $N=4.86$. Found: $C=50.14$, $H=6.33$, $N=4.77$.

EXAMPLE 7

1-N-Benzylaminomethyl-4,5-dimethoxy indane hydrochloride

A solution of 1 g. of 1-aminomethyl-4,5-dimethoxy indane hydrochloride in 100 ml. of methanol was reacted with 0.45 ml. of benzaldehyde, 0.55 g. of sodium acetate trihydrate and 0.15 g. of 5% platinum-on-carbon catalyst under 3 atmospheres of hydrogen at room temperature for 20 hours. The reaction mixture was filtered and solvents were removed from the filtrate in vacuo. The residue was dissolved in aqueous potassium hydroxide and extracted with methylene dichloride. The organic layer was separated, dried, filtered and evaporated. The resulting residue was taken up into 5 ml. of ether and then acidified with 15 ml. of ethereal hydrochloric acid, filtered and dried to obtain 1-N-benzylaminomethyl-4,5-dimethoxy indane hydrochloride; m.p. 229°–233° C.

EXAMPLE 8

1-N-Methyl-N-benzylaminomethyl-4,5-dimethoxy indane

To a solution of 1.02 g. of 1-N-benzylaminomethyl-4,5-dimethoxy indane hydrochloride in 100 ml. of methanol was added 0.416 g. of sodium acetate trihydrate, 0.5 ml. of formalin and 0.102 g. of 5% platinum-on-carbon catalyst. The reaction mixture was reacted under 3 atmospheres of hydrogen at room temperature for 6 hours. The mixture was filtered and the filtrate evaporated. The residue was dissolved in aqueous potassium hydroxide and extracted with methylene dichloride.

The organic layer was separated, dried, filtered and then evaporated in vacuo to obtain 1-N-methyl-N-benzylaminomethyl-4,5-dimethoxy indane in a 93% yield.

EXAMPLE 9

1-N-Methylaminomethyl-4,5-dimethoxy indane hydrochloride

A solution was formed of 0.75 g. of 1-N-methyl-N-benzylaminomethyl-4,5-dimethoxy indane and 0.16 g. of 5% palladium-on-carbon catalyst in 100 ml. of methanol. The solution was reacted under 3 atmospheres of hydrogen at room temperature for 1 hour. The reaction mixture was filtered and the solvent was removed from the filtrate in vacuo. The residue was taken up into 5 ml. of ether and acidified with 15 ml. of ethereal hydrochloric acid, then filtered and dried to obtain 1-N-methylaminomethyl-4,5-dimethoxy indane hydrochloride; m.p. 216°–217° C.

EXAMPLE 10

1-N-Methylaminomethyl-4,5-dihydroxy indane hydrobromide

A slurry of 0.5 g. of 1-N-methylaminomethyl-4,5-dimethoxy indane hydrochloride in 20 ml. of methylene dichloride was stirred under nitrogen at −78° C. as a solution of 0.83 ml. of boron tribromide in 3 ml. of methylene dichloride was added dropwise. The resulting solution was stirred at −78° C. for one hour and then at 0° C. for two hours. The reaction mixture was then cooled to −78° C. and 16 ml. of methanol was added dropwise. The resulting mixture was stirred at −78° C. for thirty minutes and then overnight at room temperature. The mixture was filtered, and the residue was washed with diethyl ether and dried in vacuo to obtain 1-N-methylaminomethyl-4,5-dihydroxy indane hydrobromide; m.p. 215°–217° C.

EXAMPLE 11

1-N-Acetylaminomethyl-4,5-dimethoxy indane

To a reaction mixture of 3.85 g. of 1-aminomethyl-4,5-dimethoxy indane in 40 ml. of ether at 0° C. was added 3.5 ml. of acetic anhydride. The mixture was warmed to room temperature and stirred for 1 hour. The mixture was then filtered and the residue was washed with 3 ml. of ether. The residue was dissolved in 50 ml. of methylene dichloride and 20 ml. of 1N aqueous sodium hydroxide was added to the solution. The organic layer was then separated, dried, filtered and evaporated in vacuo to obtain 3.07 g. of 1-N-acetylaminomethyl-4,5-dimethoxy indane, which was used without further purification.

EXAMPLE 12

1-N-Ethylaminomethyl-4,5-dimethoxy indane hydrochloride

To a solution of 3.07 g. of 1-N-acetylaminomethyl-4,5-dimethoxy indane in 18.5 ml. of anhydrous tetrahydrofuran was added 27.7 ml. of a 1M solution of borane in tetrahydrofuran. The solution was heated at reflux for 2 hours and then cooled to 0° C. To the solution was slowly added 40 ml. of 6N hydrochloric acid. The solution was again heated at reflux for 1 hour, then cooled to room temperature and extracted with ether. The aqueous layer was separated, made basic with a 15% aqueous solution of sodium hydroxide and extracted with 100 ml. of ether. The organic layer was separated, dried, filtered and evaporated affording a waxy residue. The residue was dissolved in 5 ml. of ether and acidified with 20 ml. of ethereal hydrochloric acid. The solution was then filtered, dried, evaporated in vacuo and recrystallized from ethanol to obtain 1.4 g. of 1-N-ethylaminomethyl-4,5-dimethoxy indane hydrochloride; m.p. 217°–218° C.

EXAMPLE 13

1-N-Ethylaminomethyl-4,5-dihydroxy indane hydrobromide

A slurry of 1.4 g. of 1-N-ethylaminomethyl-4,5-dimethoxy indane hydrobromide in 47 ml. of methylene dichloride under nitrogen was stirred at −78° C. as a solution of 3.1 ml. of boron tribromide in 5 ml. of methylene dichloride was added dropwise. The resulting reaction mixture was stirred at −78° C. for 1 hour and then at room temperature for an additional 1 hour. The reaction mixture was then cooled to −78° C., and quenched by the dropwise addition of 100 ml. of methanol. The solution was then evaporated in vacuo to dryness, and the residue was recrystallized from isopropanol to obtain 1-N-ethylaminomethyl-4,5-dihydroxy indane hydrobromide; m.p. 215°–216° C.

EXAMPLE 14

1-N,N-Diethylaminomethyl-4,5-dimethoxy indane hydrochloride

To a solution of 5.42 g. of 1-aminomethyl-4,5-dimethoxy indane in 110 ml. of methanol was added 14 ml. of acetaldehyde and 3.5 g. of sodium cyanoborohydride. The solution was stirred at room temperature overnight, acidified with 1N hydrochloric acid and then extracted with 150 ml. of a 1:1 solution of ethyl acetate and methylene dichloride. The resulting aqueous layer was made basic with a 15% aqueous solution of sodium hydroxide, and then extracted with 150 ml. of methylene dichloride. The organic layer was washed with a saturated aqueous sodium chloride solution, separated, dried, filtered and evaporated in vacuo. The resulting residue was taken up in 10 ml. of ether, acidified with 15 ml. of ethereal hydrochloric acid, and filtered. Recrystallization from isopropanol yielded 1-N,N-diethylaminomethyl-4,5-dimethoxy indane hydrochloride, m.p., 165°–167° C.

EXAMPLE 15

1-N,N-Diethylaminomethyl-4,5-dihydroxy indane hydrobromide

A slurry of 0.95 g. of 1-N,N-diethylaminomethyl-4,5-dimethoxy indane hydrochloride in 30 ml. of methylene dichloride under nitrogen was stirred at −78° C. as a solution of 1.9 ml. of boron tribromide in 5 ml. of methylene dichloride was added dropwise. The resulting reaction mixture was stirred at −78° C. for 1 hour and then at room temperature for an additional 1 hour. The reaction mixture was then cooled to −78° C., and quenched by the dropwise addition of 100 ml. of methanol. The solution was then evaporated in vacuo to dryness, and the residue was recrystallized from isopropanol to obtain 1-N,N-diethylaminomethyl-4,5-dihydroxy indane hydrobromide; m.p. 174°–176° C.

EXAMPLE 16

In Vitro Activity

The α-adrenergic receptor agonist activity of the compound of Example 6 is demonstrated in the isolated rabbit aorta as follows. Female rabbits, weighing 2 to 5 kg., are sacrificed by cervical dislocation. The thoracic cavity is immediately opened and the descending aorta is removed and placed in a petrie dish containing an aqueous buffer solution (Krebs buffer) of 119 mM NaCl, 25 mM NaHCl$_3$, 4.7 mM KCl, 1.5 mM MgSO$_4$, 1.2 mM KH$_2$PO$_4$, 2.5 mM CaCl$_2$, 11 mM glucose, 0.03 mM EDTA and 0.005 mM sodium ascorbate, adjusted to a pH of 7.4. The buffer solution is continuously aerated with a mixture of 95% O$_2$ and 5% CO$_2$ gases. The aorta is placed on cylindrical sticks and cleaned of excess fat and connective tissue, then cut into 2 tissue segments approximately 20 mm in length. Each segment of aorta is then spiraled in strips 3.5 mm wide by turning the stick as a scapel is applied, while leaving a section of 2-3 mm at each end of the aorta section intact. The spiraled tissue is mounted in an aerated (as above) tissue bath of 10 ml. of Kreb's buffer and is attached to a Grass force transducer with an initial applied tension of 2 grams. The tissue is allowed to equilibrate in the tissue bath at a temperature of 37°±0.5° C. until the tension on the force transducer stabilizes at 2 grams. A cumulative dose-response curve of contraction for the tissue is determined by contacting the tissue with 10 to 400 ul of the standard agonist norepinephrine in log doses of from $1\times10^{-8}$ to $1\times10^{-3}$M.

The tissue is washed with Krebs buffer until it relaxes to baseline tension. The tissue is then contacted with 10 to 400 ul of the test compound 1-N,N-dimethylaminomethyl-4,5-dihydroxy indane hydrobromide in a saline solution at log doses of $1\times10^{-8}$ to $1\times10^{-3}$M. The concentrations of the test compound which produces a half maximum response (ED$_{50}$) is compared with the ED$_{50}$ of norepinephrine to provide a measure of agonist potency. The percentage of the maximum increase in tension produced by the test compound over the maximum response obtained by administration of norepinephrine is the quantitative intrinsic activity of the test compound. If the intrinsic activity is greater than 75%, the compound is considered as a full agonist.

In accordance with the foregoing procedure, the compound 1-N,N-dimethylaminomethyl-4,5-dihydroxy indane hydrobromide was determined to be an α-adrenergic receptor full agonist having an ED$_{50}$ in the test aorta strip of $1.6\times10^{-6}$M.

EXAMPLE 17

In Vitro Activity

The relative selectivity of the compound of Example 6 for α$_1$- or α$_2$-adrenergic receptor sites was determined from radioligand binding data obtained in rat liver (α$_1$) and rat brain cortex (α$_2$) tissues. The dissociation constant (K$_D$) is determined for the radioligand ($^3$H) prazosin with respect to α$_1$-adrenergic receptors and for the radioligand [$^3$H] rauwolscine with respect to α$_2$-adrenergic receptors according to the method of Hoffman, et al, *Life Sciences*, Vol. 28, pp. 265-272. The concentration of the test compound (IC$_{50}$) required to displace 50% of the total specific binding of the radioligand is determined and used to calculate the nanomolar dissociation constant (KI) of the test compound for a particular α-adrenergic receptor according to the following relationship:

$$KI = \frac{IC_{50}}{1 + \frac{[L]}{K_D}}$$

where [L] is the radioligand concentration and K$_D$ is the dissociation constant for the radioligand. The KI value provides quantitative measure of the affinity of a test compound for a receptor site, with relatively lower KI values indicating relatively higher affinities.

In accordance with the foregoing procedure, the nanomolar α$_1$- and α$_2$-dissociation constants of the hydrobromide salts of compounds of the formula

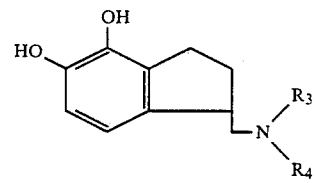

was determined, wherein R$_3$ and R$_4$ were as shown in Table I, and compared with the corresponding values for clonidine, epinephrine, and norepinephrine as shown in the following Table I:

TABLE I

| Compound | R$_3$ | R$_4$ | KIα$_1$ | KIα$_2$ | KIα$_1$/KIα$_2$ |
|---|---|---|---|---|---|
| A | CH$_3$ | CH$_3$ | 6899 | 25 | 276 |
| B | H | H | 8618 | 15 | 575 |
| C | CH$_3$ | H | 1692 | 6 | 282 |
| Clonidine | — | — | 648 | 34 | 20 |
| Epinephrine | — | — | 286 | 53 | 5 |
| Norepinephrine | — | — | 391 | 30 | 13 |

EXAMPLE 18

In Vivo Activity

The in vivo activity of 1-N,N-dimethylaminomethyl-4,5-dihydroxy indane hydrobromide was demonstrated by its ability to decrease arterial blood pressure and heart rate in the spontaneously hypertensive rat by the following procedure. Two groups of Okamoto rats, which develop hypertension spontaneously when reaching young adulthood, are deprived of food for a period of 16 hours and are placed in semirestraining wire mesh cylinders maintained at a constant temperature of 36° C. An occluding cuff, operatively connected to a programmed sphygmomanometer, is placed over the tail of each rat of the group and retained near the tail base. The pressure of each cuff is automatically cyclically increased within the range of from 0 to 250 mm Hg. at the rate of 10 mm Hg./sec., the total inflation and deflation time of each cycle being 50 seconds, with a 10 second rest period between cycles. A photocell is placed distal to the cuff to detect pulses resulting from the forward motion of blood flow with each heartbeat of the rat. As the pressure in the cuff increases, measurable pulses disappear at the point where the cuff pressure equals the arterial blood pressure. Measurable pluses reappear during deflation at approximately the same pressure, and arterial blood pressure is thereby established by cuff pressure at the point of pulse appearance. The heart rate is determined from the arterial pulse wave. Doses of 30 or 100 mg./kg. of the preferred compound of Example 6 were administered orally to each rat of the test groups and five interference-free signals were recorded on a Model 7 Grass polygraph for each rat at various measurement periods following administration. By following the foregoing procedure, the preferred compound of Example 6 was shown to decrease the arterial blood pressure of rats of each group.

The compounds of the invention can be administered in any effective pharmaceutically acceptable form to warm blooded animals, e.g., in oral, parenteral or infusable dosage forms, or as a buccal or nasal spray. Suitable parenteral routes of administration include, for example, intramuscular, administration of the compounds.

In addition to the active compounds, compositions according to this invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispensing agents. They may be sterilized, for example, by filtration through a bacteria-retaining filter, or by incorporating sterilizing agents into the compositions. They can also be manufactured in the form of sterile solid compositons which can be dissolved in sterile water, or other sterile injectable medium, immediately before use.

Solid dosage forms for oral administration include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides such inert diluents, compositions may also comprise adjuvants, such as wetting agents, emulsifying and suspending agents, and sweetening, flavoring and perfuming agents.

Actual dosage levels of active ingredient in the compositions of the invention may be varied so as to obtain an amount of active ingredient effective to obtain a desired therapeutic response for a particular composition and method of administration. The selected dosage level therefore depends upon the desired therapeutic effect, on the route of administration, on the desired duration of treatment and other factors. Generally, it is contemplated that dosage levels of about 1 to about 2000, more preferably about 5 to about 500 and most preferably about 10 to about 200 mg. of active ingredient per kg. of body weight per day administered orally will be effective in the treatment of a mammalian patient suffering from hypertension. If desired, the daily dose may be divided into multiple doses for administration, e.g., two to four separate doses per day.

What is claimed is:

1. A method of producing $\alpha_2$-adrenergic receptor agonist activity comprising administering to an animal in need of said activity production, an amount of a compound of the formula

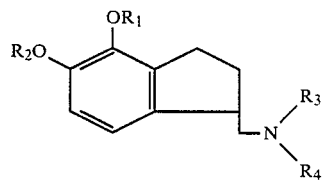

wherein $R_1$, $R_2$, $R_3$ and $R_4$ are independently selected from hydrogen or loweralkyl of 1 to 2 carbon atoms, or a pharmaceutically acceptable salt thereof, sufficient to produce said activity.

2. A method of treating hypertension comprising administering to an animal in need of said treatment an antihypertensively effective amount of a compound of the formula

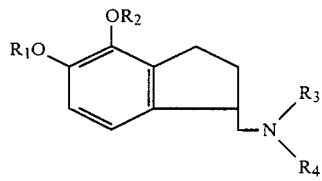

wherein $R_1$, $R_2$, $R_3$ and $R_4$ are independently selected from hydrogen and loweralkyl of 1 to 2 carbon atoms, or a pharmaceutically acceptable salt thereof.

3. A method of claim 1 or 2 wherein $R_1$ and $R_2$ are hydrogen.

4. A method of claim 3 wherein $R_3$ and $R_4$ are hydrogen.

5. A method of claim 3 wherein $R_3$ is hydrogen and $R_4$ is methyl.

6. A method of claim 3 wherein $R_3$ and $R_4$ are methyl.

* * * * *